United States Patent [19]

Zaiger et al.

[11] Patent Number: Plant 6,347

[45] Date of Patent: Oct. 25, 1988

[54] PEACH TREE ("TRA-ZEE")

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 945,942

[22] Filed: Dec. 24, 1986

[51] Int. Cl.[4] ..... A01H 5/03

[52] U.S. Cl. ..... Plt./43

[58] Field of Search ..... Plt. 43

*Primary Examiner*—Robert E. Bagwill

[57] ABSTRACT

The present variety of peach tree is of large size, vigorous, upright growth and a regular and productive bearer of large, firm, yellow flesh, freestone fruit, being late in maturity and the yellow skin substantially overspread with an attractive light red blush. The fruit is further characterized by its good flavor and eating quality and its ability to ship to long distance markets.

1 Drawing Sheet

ORIGIN OF THE VARIETY

The new variety of peach tree was originated by us in the experimental orchard located near Modesto, Calif. as a first generation seedling of a cross between a late maturing nectarine of unknown parentage and a late maturing peach which originated from a selection of open pollinated O'Henry Peach (U.S. Plant Pat. No. 2,964) seedlings.

ASEXUAL REPRODUCTION OF THE VARIETY

The present variety of peach tree was asexually reproduced by budding, as performed by us in the experimental orchard located at Modesto, Calif. and shows that said characteristics come true to form and are established and transmitted through succeeding propagations.

SUMMARY OF THE VARIETY

The present new and distinct variety of peach tree; its novelty consists of the following unique features which are outstanding in a new variety:

1. Ability to produce fruit with a high degree of attractive light red blush in the late maturity season.
2. Large fruit size.
3. Fruit with good flavor and eating quality.
4. The ability of the fruit to stay firm on the tree 8–10 days after maturity (shipping ripe).
5. Uniform ripening of the fruit throughout the tree.
6. The fruit having good storage and shipping quality.
7. Fruit maturing in late season approximately 21 days after O'Henry Peach (U.S. Plant Pat. No. 2,964).

DESCRIPTION OF THE PHOTOGRAPHS

The accompanying photographs show typical specimens of the fruit and foliage of our new peach variety. The upper and lower surface of the foliage being illustrated, the exterior and a fruit divided on its suture plane to reveal flesh, flesh cavity and stone coloration. The photographs were taken shortly after being picked (shipping ripe) and colors are as nearly true as is reasonably possible in a color representation of this type.

DESCRIPTION OF THE VARIETY

The following is a botanical description of the new and distinct variety of peach tree, its flowers, foliage and fruit as based on observations of specimens grown near Modesto, Calif., with color terminology (except those in common terms) in accordance with Reinhold color Atlas by A. Kornerup and J. H. Wanscher.

Tree:
- *Size.*—Large.
- *Vigor.*—Vigorous.
- *Form.*—Upright.
- *Density.*—Medium dense.
- *Shape.*—Usually pruned to vase shape.
- *Production.*—Productive.
- *Bearing.*—Regular.

Trunk:
- *Size.*—Medium stocky.
- *Texture.*—Medium shaggy.

Branches:
- *Size.*—Medium to large.
- *Texture.*—Smooth to medium rough.
- *Lenticels.*—Medium number. Medium size.
- *Color.*—Brown to grayish brown.

Leaves:
- *Size.*—Large. Average length — 6½" to 7". Average width — 1½".
- *Texture.*—Smooth.
- *Petiole.*—Medium length.
- *Form.*—Lanceolate. Pointed.
- *Margin.*—Crenate.
- *Glands.*—Reniform. Large. Number varies from 1 to 4. Average number 3.
- *Color.*—Upper surface — dark green (29-F-6) to (29-F-7). Lower surface — grayish green (28-E-5) to (28-E-6).

Flower buds:
- *Size.*—Medium.
- *Form.*—Plump.
- *Pubescence.*—Pubescent.

Flowers:
- *Size.*—Large — showy.
- *Pollen.*—Present.
- *Color.*—Pink.
- *Blooming period.*—Feb. 27, 1985 to Mar. 8, 1985. Varies slightly with climatic conditions.

Fruit:
- *Maturity when described.*—Firm ripe.
- *Date of first picking.*—Aug. 25, 1985.
- *Date of last picking.*—Aug. 30, 1985.

*Size.*—Large. Average diameter axially — $2\frac{7}{8}''$ to $3\frac{1}{4}''$. Average transversely in suture plane $2\frac{7}{8}''$ to $3\frac{1}{4}''$.

*Form.*—Globose — nearly symmetrical.

*Suture.*—Shallow, slightly lipped, extends from base to apex.

*Base.*—Retuse.

*Cavity.*—Rounded to slightly elongated in suture plane. Average depth — $\frac{1}{2}''$. Average breadth — $1''$.

*Apex.*—Rounded to slight depression.

Flesh:

*Color.*—Dark yellow (4-A-8) to cadmium orange (5-A-7) except intense red next to pit (10-A-8) to (10-B-8) and a lighter red (10-A-5) to (10-A-7) as the distance increases from the pit toward the skin.

*Texture.*—Firm.

*Fibers.*—Few — tender.

*Ripens.*—Evenly.

*Flavor.*—Mild — good balance between acid and sugar.

*Juice.*—Moderate.

*Aroma.*—Moderate.

*Eating quality.*—Good.

Skin:

*Thickness.*—Medium.

*Texture.*—Medium — tenacious to flesh when firm ripe. Free when soft ripe.

*Tendency to crack.*—None.

*Down.*—Moderate. Medium length.

*Color.*—Bright yellow ground color (4-A-8) to (5-A-8). Overspread with light red blush (8-A-8) to (9-B-7).

Stone:

*Type.*—Freestone.

*Size.*—Large. Average length — $1\frac{1}{2}''$. Average width — $1''$. Average thickness — $\frac{3}{4}''$.

*Form.*—Ovid.

*Base.*—Mostly straight — some rounded.

*Apex.*—Acuminate.

*Side.*—Equal to unequal.

*Surface.*—Irregularly furrowed toward apex, pitted toward base.

*Tendency to split.*—Very slight.

*Color.*—Light brown to brown (8-C-5) to (8-D-5).

Use: Dessert.

*Market.*—Local and long distance.

Keeping quality: Good.

Shipping quality: Good.

The present variety of peach tree and its fruit herein described as grown under the ecological conditions near Modesto, Calif., the variety may vary in slight detail due to different climatic, soil conditions and cultural practices under which the variety may be grown.

We claim:

1. A new and distinct variety of peach tree which is of large size, vigorous, upright in growth and being a regular and productive bearer of large, firm, yellow flesh, freestone fruit with good eating, shipping and storage quality: the fruit is further characterized by its ability to hold firm on the tree 8–10 days after maturity (shipping ripe) and maturing in the late season, approximately 21 days after O'Henry Peach (U.S. Plant Pat. No. 2,964), the yellow skin substantially overspread with an attractive light red blush.

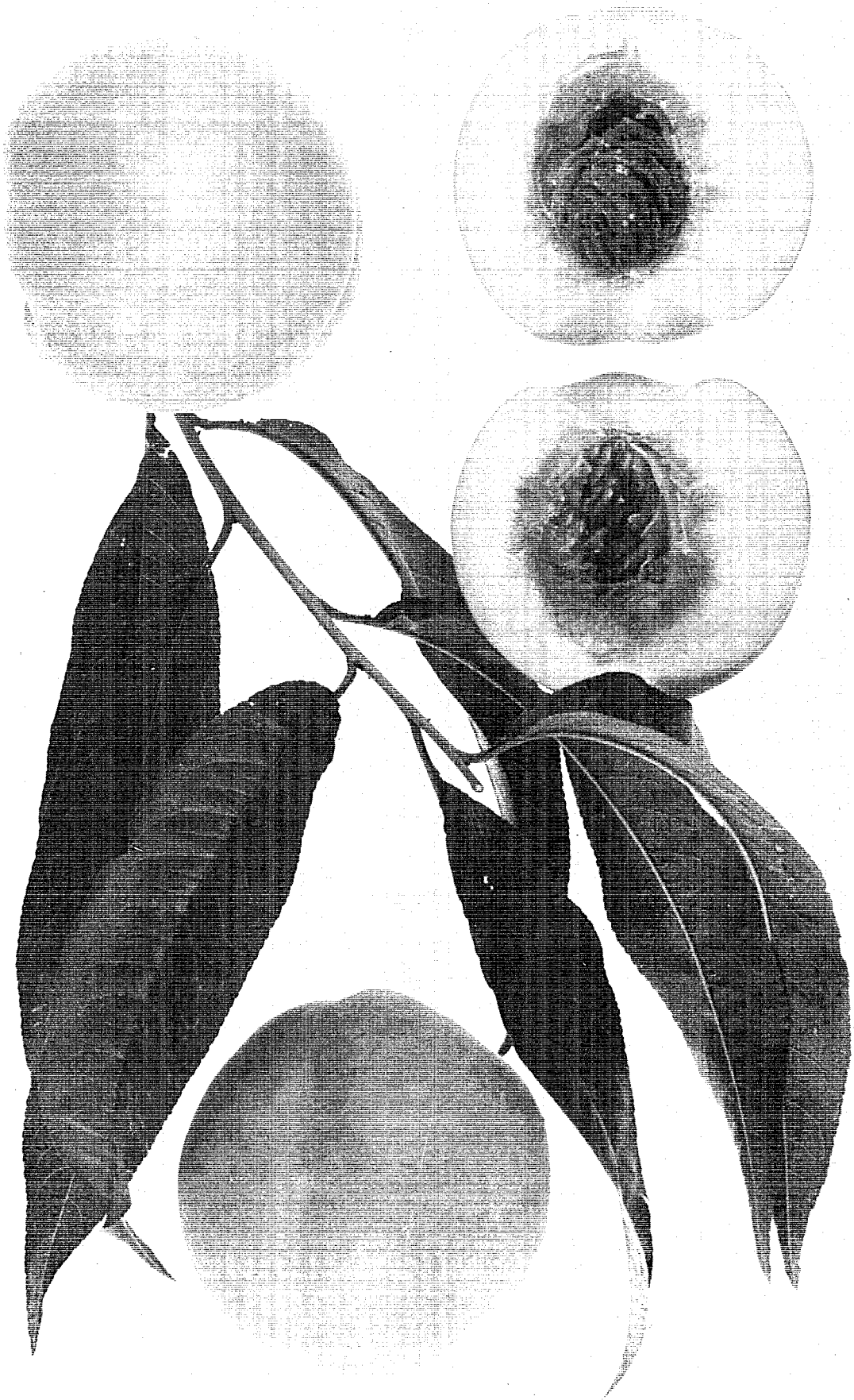

* * * * *